US007223585B2

(12) United States Patent
Coffey

(10) Patent No.: US 7,223,585 B2
(45) Date of Patent: May 29, 2007

(54) VIRAL PURIFICATION METHODS

(75) Inventor: Matthew C. Coffey, Calgary (CA)

(73) Assignee: Oncolytics Biotech Inc., Calgary (CA)

( * ) Notice: Subject to any disclaimer, the term of this patent is extended or adjusted under 35 U.S.C. 154(b) by 169 days.

(21) Appl. No.: 10/424,985

(22) Filed: Apr. 29, 2003

(65) Prior Publication Data
US 2004/0005693 A1    Jan. 8, 2004

Related U.S. Application Data

(60) Provisional application No. 60/443,176, filed on Jan. 29, 2003, provisional application No. 60/377,273, filed on Apr. 30, 2002.

(51) Int. Cl.
*C12N 7/01*    (2006.01)
*C12N 7/02*    (2006.01)
*A61K 48/00*    (2006.01)

(52) U.S. Cl. .................. 435/239; 435/235.1; 435/325; 435/369

(58) Field of Classification Search ............... 424/93.1, 424/215.1, 204.1; 435/320.1
See application file for complete search history.

(56) References Cited

U.S. PATENT DOCUMENTS

| | | | | |
|---|---|---|---|---|
| 5,403,484 A | * | 4/1995 | Ladner et al. ............ | 435/235.1 |
| 5,658,779 A | * | 8/1997 | Krupey et al. ............... | 435/239 |
| 5,731,187 A | | 3/1998 | Fanget et al. | |
| 5,948,441 A | * | 9/1999 | Lenk et al. .................. | 424/489 |
| 6,194,191 B1 | * | 2/2001 | Zhang et al. ................ | 435/239 |
| 6,726,907 B1 | * | 4/2004 | Zhang et al. ............... | 424/93.2 |
| 6,808,916 B2 | * | 10/2004 | Coffey et al. ............... | 435/238 |
| 2002/0168764 A1 | * | 11/2002 | Coffey et al. ............... | 435/325 |
| 2004/0152183 A1 | * | 8/2004 | O'Riordan et al. ......... | 435/239 |

FOREIGN PATENT DOCUMENTS

| | | |
|---|---|---|
| JP | 63044532 A | 2/1988 |
| WO | WO 97/08298 | 3/1997 |
| WO | WO 98/22588 | 5/1998 |
| WO | WO 99/08692 * | 2/1999 |
| WO | WO99/08692 A1 | 2/1999 |

OTHER PUBLICATIONS

Vellekamp et al. Hum. Gene Therapy. Oct. 10, 2001; 12:1923-36.*
Nibert et al. J. Virology. 1996; 70(10):7295-7300.*
Liu et al., Investigative Ophthalmology and Visual Science 2006, 47(6):2438-2444.*
Nooteboom et al., Clinical and Experimental Immunology 2006, 144:362-369.*
Hartwig et al., Transfusion Medicine 2005, 15:107-113.*
U.S. Appl. No. 20020037576, published Mar. 28, 2002.
Berry et al., Biotechnology and Bioengineering, "Production of Reovirus Type-1 and Type-3 from Vero Cells Grown on Solid and Macroporous Microcarriers", *Biotechnology and Bioengineering* 62: 12-19 (1999).
Bos, J.L., "Ras Oncogenes in Human Cancer: A Review", *Canc. Res.* 49(17): 4682-4689 (1989).
Chandran and Nibert, "Protease cleavage of reovirus capsid protein mu1 and mu1C blocked by alkyl sulfate detergents, yielding a new type of infectious subvirion particle", *J. of Virology* 72(1):467-75 (1998).
Coffey, M.C., et al., "Reovirus therapy of tumors with activated Ras pathway", *Science* 282: 1332-1334 (1998).
Drastini, Y. et al., "Comparison of eight different procedures for harvesting avian reoviruses grown in Vero cells", *J. Virological Methods* 39: 269-278 (1992).
Duncan et al., "Conformational and functional analysis of the C-terminal globular head of the reovirus cell attachment protein", *Virology* 182(2):810-9 (1991).
Mah et al., "The N-terminal quarter of reovirus cell attachment protein sigma 1 possesses intrinsic virion-anchoring function", *Virology* 179(1):95-103 (1990).
McRae, M.A. and Joklik, W.K., "The nature of the polypeptide encoded by each of the 10 double-stranded RNA segments of reovirus type 3", *Virology*, 89:578-593 (1979).
Nibert et al., "Reovirus and their replication", in Fields et al., *Fundamental Virology*, 3rd Edition, Lippincott-Raven (1996).
Smith, R.E., et al., "Polypeptide components of virions, top component and cores of reovirus type 3", *Virology*, 39:791-800 (1969).
Strong, J.E. and P.W. Lee, "The v-erbV oncogene confers enhanced cellular susceptibility to reovirus infection", *J. Virol.* 70: 612-616 (1996).
Strong, J.E., et al., "Evidence that the Epidermal Growth Factor Receptor on Host Cells Confers Reovirus Infection Efficiency", *Virology* 197(1): 405-411 (1993).
Strong, J.E., et al., "The molecular basis of viral oncolysis: usurpation of the Ras signaling pathway by reovirus", *EMBO J.* 17: 3351-3362 (1998).
Taber et al., "The selection of virus-resistant Chinese hamster ovary cells", *Cell* 8: 529-533 (1976).
Turner and Duncan, "Site directed mutagenesis of the C-Terminal portion of reovirus protein sigmal: evidence for a conformation-dependent receptor binding domain", *Virology* 186(1):219-27 (1992).

* cited by examiner

*Primary Examiner*—David Guzo
(74) *Attorney, Agent, or Firm*—Fish & Richardson P.C.

(57) ABSTRACT

The present invention is directed to an improved method of purifying virus, particularly reovirus. Infectious virus can be extracted from a cell culture with a detergent to produce high titers of virus, and the virus can then be purified by simple steps such as filtration and column chromatography. Viruses and compositions comprising the viruses prepared according to the present invention are also provided.

14 Claims, No Drawings

VIRAL PURIFICATION METHODS

RELATED APPLICATIONS

This application claims the benefit of U.S. Provisional Applications Ser. No. 60/377,273, filed Apr. 30, 2002; and Ser. No. 60/443,176, filed Jan. 29, 2003. The entire disclosure of these prior applications is hereby incorporated by reference.

FIELD OF THE INVENTION

This invention relates to a method of extracting virus from a cell culture. In particular, the method is useful for extracting infectious virus which is suitable for clinical administration to mammals, including human.

REFERENCES

U.S. Patent Application Publication No. 20020037576, published Mar. 28, 2002.

WO99/08692A1, published Feb. 25, 1999.

Japanese Patent 63044532A, published Feb. 25, 1988.

Berry et al., Biotechnology and Bioengineering, "Production of Reovirus Type-1 and Type-3 from Vero Cells Grown on Solid and Macroporous Microcarriers", *Biotechnology and Bioengineering* 62: 12–19 (1999).

Bos, J. L., "Ras Oncogenes in Human Cancer: A Review", *Canc. Res.* 49(17): 4682–4689 (1989).

Chandron and Nibert, "Protease cleavage of reovirus capsid protein mu1 and mu1C is blocked by alkyl sulfate detergents, yielding a new type of infectious subvirion particle", *J. of Virology* 72(1):467–75 (1998).

Coffey, M. C., et al., "Reovirus therapy of tumors with activated Ras pathway", *Science* 282: 1332–1334 (1998).

Davis, et al., *Microbiology*, Lippincott, Philadelphia (1990).

Drastini, Y. et al., "Comparison of eight different procedures for harvesting avian reoviruses grown in Vero cells", *J. Virological Methods* 39: 269–278 (1992).

Duncan et al., "Conformational and functional analysis of the C-terminal globular head of the reovirus cell attachment protein", *Virology* 182(2):810–9 (1991).

Fields, B. N. et al., *Fundamental Virology*, 3rd Edition, Lippincott-Raven (1996).

Mah et al., "The N-terminal quarter of reovirus cell attachment protein sigma 1 possesses intrinsic virion-anchoring function", *Virology* 179(1):95–103 (1990).

McRae, M. A. and Joklik, W. K., "The nature of the polypeptide encoded by each of the 10 double-stranded RNA segments of reovirus type 3", *Virology*, 89:578–593 (1979).

Nibert et al., "Reovirus and their replication", in Fields et al., *Fundamental Virology*, 3rd Edition, Lippincott-Raven (1996).

*Remington's Pharmaceutical Sciences*, Mack Publishing Company, Philadelphia Pa. 19$^{th}$ ed. (1995).

Smith, R. E., et al., "Polypeptide components of virions, top component and cores of reovirus type 3", *Virology*, 39:791–800 (1969).

Strong, J. E. and P. W. Lee, "The v-erbV oncogene confers enhanced cellular susceptibility to reovirus infection", *J. Virol.* 70: 612–616 (1996).

Strong, J. E., et al., "Evidence that the Epidermal Growth Factor Receptor on Host Cells Confers Reovirus Infection Efficiency", *Virology* 197(1): 405–411 (1993).

Strong, J. E., et al., "The molecular basis of viral oncolysis: usurpation of the Ras signaling pathway by reovirus", *EMBO J.* 17: 3351–3362 (1998).

Taber et al., "The selection of virus-resistant Chinese hamster ovary cells", *Cell* 8: 529–533 (1976).

Turner and Duncan, "Site directed mutagenesis of the C-terminal portion of reovirus protein sigma1: evidence for a conformation-dependent receptor binding domain", *Virology* 186(1):219–27 (1992).

All of the publications, patents and patent applications cited above or elsewhere in this application are herein incorporated by reference in their entirety to the same extent as if the disclosure of each individual publication, patent application or patent was specifically and individually indicated to be incorporated by reference in its entirety.

BACKGROUND OF THE INVENTION

Due to the vast number of diseases caused by viruses, virology has been an intensively studied field. There has always been the demand to produce viruses efficiently in order to isolate and purify viral proteins, to generate vaccines, or to provide infectious viruses for laboratory studies. Recently, the new development of virus therapy has further necessitated the need for efficient production of infectious viruses.

Reovirus therapy is an example of virus therapy. Reovirus is a double-stranded RNA virus capable of binding to a multitude of cells. However, most cells are not susceptible to reovirus infection and binding of reovirus to its cellular receptor results in no viral replication or virus particle production in these cells. This is probably the reason why reovirus is not known to be associated with any particular disease.

It was discovered recently that cells transformed with the ras oncogene become susceptible to reovirus infection, while their untransformed counterparts are not (Strong et al., 1998). For example, when reovirus-resistant NIH 3T3 cells were transformed with activated Ras or Sos, a protein which activates Ras, reovirus infection was enhanced. Similarly, mouse fibroblasts that are resistant to reovirus infection became susceptible after transfection with the EGF receptor gene or the v-erbB oncogene, both of which activate the ras pathway (Strong et al., 1993; Strong et al., 1996). Thus, reovirus can selectively infect and replicate in cells with an activated Ras pathway.

The ras oncogene accounts for a large percentage of mammalian tumors. Activating mutations of the ras gene itself occur in about 30% of all human tumors (Bos, 1989), primarily in pancreatic (90%), sporadic colorectal (50%) and lung (40%) carcinomas, as well as myeloid leukemia (30%). Activation of factors upstream or downstream of ras in the ras pathway is also associated with tumor. For example, overexpression of HER2/Neu/ErbB2 or the epidermal growth factor (EGF) receptor is common in breast cancer (25–30%), and overexpression of platelet-derived growth factor (PDGF) receptor or EGF receptor is prevalent in gliomas and glioblastomas (40–50%). EGF receptor and PDGF receptor are both known to activate ras upon binding to their respective ligand, and v-erbB encodes a constitutively activated receptor lacking the extracellular domain.

Since a large number of human tumors are accounted for by genetic alteration of the proto-oncogene ras or a high Ras activity, reovirus therapy is a new, promising therapy for such conditions (Coffey et al., 1998). Reovirus therapy is highly selective for Ras-associated tumor cells and leaves normal cells uninfected. This therapy has wide applications and can be used in both human and non-human animals.

In order to produce reovirus suitable for clinical administration, fast and efficient methods of producing reovirus in cultured cells are needed. Moreover, the traditional method of purifying viruses from cultured cells is tedious and time consuming, rendering the cost of virus production too high. Therefore, an improved method for virus purification is also needed.

SUMMARY OF THE INVENTION

The present invention relates to an improved method of extracting and purifying viruses from cell culture that can be applied to both small and large scale virus production. The method involves a simple extraction step in which a detergent is directly added to the cell culture. Thereafter, cell debris can be removed from the extraction mixture by, for example, filtration or centrifugation. The resulting virus suspension can be further concentrated and/or enriched by chromatographic methods. The virus prepared according to the present invention can be used for any purpose, including purification of viral proteins, vaccination, infection of host cells and clinical administration.

Accordingly, one aspect of the present invention provides a method of producing virus from a culture of cells, comprising the steps of:

(a) providing a culture of cells which has been infected by the virus;
(b) extracting the virus from the cells by adding a detergent to the culture and incubating for a period of time to result in a cell lysate;
(c) removing cell debris; and
(d) collecting the virus.

Any method can be used to remove cell debris (i.e., clarify the cell lysate) in step (c). The method is preferably a simple method based on the size or density differences between the virus and the other constituents in the cell lysate, such as filtration or centrifugation. More preferably, filtration is employed, particularly step-wise filtration. An appropriate step-wise filtration comprises a prefilter having a larger pore size, followed by at least another filter with a pore size smaller than that of the prefilter. In a preferred embodiment, the cell debris is removed by step-wise filtration comprising:

(1) filtering through a prefilter having a pore size of 5 µM or 8 µM, and
(2) filtering after step (1) through a combination filter having pore sizes of 3 µM and 0.8 µM.

The cell lysate can optionally be treated with BENZONASE® endonuclease or other DNA-cleaving enzyme to break up long, viscous cellular DNA.

After removing cell debris by filtration, the filtrate can optionally be concentrated to reduce the volume of the viral suspension. Any methods suitable for viral concentration can be employed, preferably ultrafiltration or diafiltration, including tangential flow filtration. Exemplary methods include the Plate and Frame system and the Hollow Fiber system. More preferably, the Hollow Fiber system is used.

The present method can be applied in the production of any virus, preferably a non-enveloped virus, and most preferably a reovirus. The reovirus is preferably a mammalian reovirus, more preferably a human reovirus, still more preferably a serotype 3 reovirus, and most preferably a Dearing strain reovirus. The reovirus may be a recombinant reovirus. The recombinant reovirus may be generated by co-infection of cells, such as mammalian cells or avian cells, with different subtypes of reovirus. The recombinant reovirus may be naturally-occurring or non-naturally-occurring. The recombinant reovirus may be from two or more strains of reovirus, particularly two or more strains of reovirus selected from the group consisting of strain Dearing, strain Abney, strain Jones, and strain Lang. The recombinant reovirus may also result from reassortment of reoviruses from different serotypes, such as selected from the group consisting of serotype 1 reovirus, serotype 2 reovirus and serotype 3 reovirus. The recombinant reovirus may comprise naturally-occurring variant coat protein coding sequences or mutated coat protein coding sequences.

The cell culture used in the present invention can comprise any cell appropriate for the production of the desired virus. For reovirus, the cell is preferably human embryo kidney 293 (HEK 293) cells or cells derived thereof, particularly HEK 293 cells that have been adapted to grow in suspension cultures.

The method can optionally comprise a step of ion exchange chromotography, wherein the virus is enriched by binding to an ion exchange resin under appropriate binding and conditions. the virus is then eluted from the ion exchanger using a suitable elution solution. The choice of ion exchanger and binding/elution conditions will vary with the virus being purified. For reovirus, an anion exchanger and pH of approximately 7.0–9.0 are the most effective. The pH is preferably about 7.5 to about 8.5, and most preferably about 8.0.

The virus can also be purified by using size exclusion chromatography. In particular, a combination of ion exchange and size exclusion chromatography can be employed.

Another aspect of the present invention provides a composition comprising the virus purified according to any of the methods described herein. The composition is preferably suitable for clinical administration, particularly clinical administration to human. More preferably, the composition comprises a pharmaceutically acceptable excipient and/or carrier.

Another aspect of the present invention provides a method of producing infectious reovirus, comprising:

(a) providing a culture of HEK 293 cells which has been infected by reovirus;
(b) extracting the virus from the cells by adding TRITON® X-100 (octoxynol-9 to 10) to the culture and incubating at about 25° C. to about 37° C.;
(c) treating the mixture from step (b) with BENZONASE® endonuclease;
(d) removing cell debris by filtration;
(e) concentrating the filtrate by ultrafiltration or diafiltration;
(f) purifying the reovirus by a combination of ion exchange and size exclusion chromatography; and
(g) collecting the reovirus.

Also provided are compositions comprising the reovirus collected according to this method, particularly compositions further comprising a pharmaceutically acceptable excipient and/or carrier.

DETAILED DESCRIPTION OF THE INVENTION

The present invention relates to an improved method of extracting and purifying viruses from cell culture that can be applied to both small and large scale virus production. The method involves a simple extraction step in which a detergent is directly added to the cell culture. Thereafter, cell debris can be removed from the extraction mixture by, for example, filtration or centrifugation. The resulting virus suspension can be further concentrated and/or enriched by chromatographic methods. The virus prepared according to the present invention can be used for any purpose, including purification of viral proteins, vaccination, infection of host cells and clinical administration.

Prior to describing the invention in further detail, the terms used in this application are defined as follows unless otherwise indicated.

Definitions

As used herein, "viral infection" refers to the entry of a virus into a cell and the subsequent replication of the virus in the cell.

As used herein, "multiplicity of infection" refers to the ratio of the number of virus to the number of cells when a virus is used to contact cells.

As used herein, "cell lysis" refers to the disruption of cell membrane of a cell and the subsequent release of all or part of the content of the cell.

As used herein, "culture conditions" refer to the conditions used in a cell culture, including but not limited to the temperature, type of culture containers, humidity, concentration of $CO_2$ or any other gas used in the culture containers, type of the culture medium, the initial density of the cultured cells, and if the cells are infected with a virus, the initial multiplicity of infection.

As used herein, a "cell culture" or "culture of cells" means a population of cultured cells as found in their culture conditions. In particular, a cell culture includes the cells and the culture medium. Cells that have been pelleted are not considered a cell culture unless they are placed in culture medium under culture conditions again.

As used herein, a virus that is "cell associated" refers to a virus which is attached to or trapped in part of a cell in which the virus has been produced. Thus, a virus is cell associated before the host cell is lysed. When cell lysis begins, a virus may be still attached to or trapped in part of the broken cell and remain cell associated. However, when the virus is released free into the medium, it is not cell associated anymore. A "cell free virus" is a virus which is not cell associated.

As used herein, "extracting" a virus refers to the act of converting a cell associated virus into a cell free virus.

As used herein, a "detergent" is a substance having a hydrophilic end and a hydrophobic end. The detergent is preferably a synthetic chemical compound and more preferably a biodegradable synthetic chemical compound. The detergent useful in the present invention enhances disruption of cell membranes to facilitate release of the content of the disrupted cells.

As used herein, "incubating" after addition of a detergent to a cell culture refers to the act of allowing the cell culture to be mixed with the detergent for a period of time.

As used herein, "collecting" the virus refers to the act of collecting the virus produced from a cell culture which has been previously infected with the virus. The virus is typically collected by separating cellular debris from the virus and harvesting the portion which comprises the virus. Optionally, the virus can be further separated from the soluble substances, e.g., by centrifugation.

As used herein, "ambient temperature" refers to a temperature between about 10° C. and about 30° C. Ambient temperature is preferably between about 15° C. and about 30° C., more preferably between about 20° C. and about 25° C., and most preferably about 25° C.

As used herein, "cytopathic effect" is indicated by the cells becoming swollen and granular in appearance and the cell clumps breaking up. Cells which show a cytopathic effect also take up the staining dye in a viable cell count.

As used herein, "adherent cells" refer to cells which adhere to the culture containers in a cell culture. Examples of adherent cells include monolayer cells, which are cells that form a single layer of cells on the surface of a culture container. "Suspension cells" or "suspended cells" refer to cells which do not adhere to culture containers in a cell culture. Suspension cells can be grown in a "spin culture", which is a culture in which the culture medium is stirred continuously during the culture process.

As used herein, a cell is "disrupted" when the cell membrane is ruptured and at least some of the cell content is released from the cell. A cell may be disrupted, for example, by freeze-thawing, sonication or detergent treatments.

As used herein, "viability of the cells" or "percentage of cells remaining viable" is the percentage of the cells which do not show a cytopathic effect in a population.

As used herein, a "non-enveloped virus" is a virus which does not have an envelope. For example, a non-enveloped virus may be any virus which belongs to the family of Adenoviridae (e.g. adenovirus), Picornaviridae (e.g. polio virus), Reovirudae (e.g. reovirus), Papovarviridae (e.g. papilloma virus), Parvoviridae (e.g. Kilham rat virus) or Iridoviridae (e.g. tipula iridescent virus).

As used herein, "reovirus" refers to any virus classified in the reovirus genus, whether naturally occurring, modified or recombinant. Reoviruses are viruses with a double-stranded, segmented RNA genome. The virions measure 60–80 nm in diameter and possess two concentric capsid shells, each of which is icosahedral. The genome consists of double-stranded RNA in 10–12 discrete segments with a total genome size of 16–27 kbp. The individual RNA segments vary in size. Three distinct but related types of reovirus have been recovered from many species. All three types share a common complement-fixing antigen.

The human reovirus consists of three serotypes: type 1 (strain Lang or T1L), type 2 (strain Jones, T2J) and type 3 (strain Dearing or strain Abney, T3D). The three serotypes are easily identifiable on the basis of neutralization and hemagglutinin-inhibition assays (see, for example, Fields, B. N. et al., 1996).

The reovirus may be naturally occurring or modified. The reovirus is "naturally-occurring" when it can be isolated from a source in nature and has not been intentionally modified by humans in the laboratory. For example, the reovirus can be from a "field source", that is, from a human who has been infected with the reovirus.

The reovirus may be modified but still capable of lytically infecting a mammalian cell having an active ras pathway. The reovirus may be chemically or biochemically pretreated (e.g., by treatment with a protease, such as chymotrypsin or trypsin) prior to administration to the proliferating cells. Pretreatment with a protease removes the outer coat or capsid of the virus and may increase the infectivity of the virus. The reovirus may be coated in a liposome or micelle (Chandron and Nibert, 1998). For example, the virion may be treated with chymotrypsin in the presence of micelle forming concentrations of alkyl sulfate detergents to generate a new infectious subvirion particle.

The reovirus may be a recombinant reovirus resulting from the recombination/reassortment of genomic segments from two or more genetically distinct reoviruses. Recombination/reassortment of reovirus genomic segments may occur in nature following infection of a host organism with at least two genetically distinct reoviruses. Recombinant virions can also be generated in cell culture, for example, by co-infection of permissive host cells with genetically distinct reoviruses (Nibert et al. 1995).

Accordingly, the invention contemplates the recombinant reovirus resulting from reassortment of genome segments from two or more genetically distinct reoviruses, including but not limited to, human reovirus, such as type 1 (e.g., strain Lang), type 2 (e.g., strain Jones), and type 3 (e.g., strain Dearing or strain Abney), non-human mammalian reoviruses, or avian reovirus. The invention further contemplates recombinant reoviruses resulting from reassortment of genome segments from two or more genetically distinct reoviruses wherein at least one parental virus is genetically engineered, comprises one or more chemically synthesized genomic segment, has been treated with chemical or physical mutagens, or is itself the result of a recombination event. The invention further contemplates the recombinant reovirus that has undergone recombination in the presence of chemical mutagens, including but not limited to dimethyl sulfate and ethidium bromide, or physical mutagens, including but not limited to ultraviolet light and other forms of radiation.

The invention further contemplates recombinant reoviruses that comprise deletions or duplications in one or more genome segments, that comprise additional genetic information as a result of recombination with a host cell genome, or that comprise synthetic genes.

The reovirus may be modified by incorporation of mutated coat proteins, such as for example σ1, into the virion outer capsid. The proteins may be mutated by replacement, insertion or deletion. Replacement includes the insertion of different amino acids in place of the native amino acids. Insertions include the insertion of additional amino acid residues into the protein at one or more locations. Deletions include deletions of one or more amino acid residues in the protein. Such mutations may be generated by methods known in the art. For example, oligonucleotide site directed mutagenesis of the gene encoding for one of the coat proteins could result in the generation of the desired mutant coat protein. Expression of the mutated protein in reovirus infected mammalian cells in vitro such as COS1 cells will result in the incorporation of the mutated protein into the reovirus virion particle (Turner and Duncan, 1992; Duncan et al., 1991; Mah et al., 1990).

As used herein, "HEK 293 cells" refer to the human embryo kidney cell line designated 293 (ATCC Number CRL-1573) or its derivatives. For example, 293/SF cells (ATCC Number CRL-1573.1) are HEK 293 cells which have been adapted to grow in serum-free media. Also contemplated in this invention are HEK 293 cells adapted to grow in other culture conditions, or any kind of HEK 293 cells or derivatives which are transformed with an exogenous DNA, provided that this transformation does not impair the ability of the cells to support efficient reovirus production as described in this invention.

As used herein, "clinical administration" of a substance refers to contacting any part of the body of a living organism with the substance in order to improve or maintain the organism's health conditions.

Methods

We have previously developed a method of growing reovirus in HEK 293 cells (U.S. Patent Application Publication No. 20020037576). Reovirus replicates in HEK 293 cells to yield a high titer of virus in the cells shortly after virus infection, thereby providing a simple and efficient method of producing reovirus. In addition, HEK 293 cells has been adapted to grow in suspension which can be cultured in large quantity, and we developed a large scale production method. To isolate reovirus from the suspension culture, we initially followed traditional methods to extract and purify viral particles. Briefly, the cells were disrupted by freeze-thawing and extracted by FREON® (1,1,2-trichloro-1,1,2-trifluoro-ethane) three times. The viral particles were then purified with a CsCl gradient and ultracentrifugation. However, this protocol was too tedious and time consuming for large scale virus production.

We therefore developed a simplified method to extract the reovirus. It was discovered that by incubating the HEK 293 cell culture with a detergent for a short period of time, high levels of infectious reovirus were released to the extract. The virus can then be separated from the cell debris with a simple separation method based on size or density differences, such as filtration, diafiltration or size exclusion, and the resulting virus can be used for reovirus therapy. The reovirus produced according to the present invention is suitable for administration in human, and this protocol is consistent with the FDA recommendation of disrupting cells in the presence of a detergent.

We tested four detergents in a preliminary experiment, the non-ionic detergents octoxynol-9 to 10 (TRITON® X-100), octylphenoxy polyethoxy ethanol (NONIDETTM™ P40 or NP-40) and polyethylene glycol sorbitan monolaurate (TWEEN® 20), as well as the ionic detergent sodium deoxycholate. All four detergents were capable of lysing the cells and releasing infectious viral particles above the background level, and TRITON® X-100 was the most effective. It is contemplated that other detergents, particularly the ones commonly used to disrupt cells, can be used in the present invention as well. Examples of these other detergents include the other TRITON® detergents, the other TWEENT® detergents (e.g. polyoxyethylene sorbitan monooleate TWEEN® 80 ), sodium dodecyl sulfate, lithium dodecyl sulfate, and dodecyltrimethylammonium chloride.

The results also indicate that detergent extraction can be more effective than freeze-thawing, the standard procedure for virus extraction. In addition, it has been reported that to extract avian reovirus from Vero cells in which the reovirus is highly cell associated, distilled deionized water was more effective than freeze-thawing, FREON® (1,1,2-trichloro-1,1,2-trifluoro-ethane) extraction or trypsin treatment (Drastini et al., 1992). The present invention provides a more rapid and convenient yet effective approach, because there is no need to pellet and then resuspend the cells as required by the distilled water method.

It is contemplated that high concentrations of salt, such as guanidine chloride, can be used in the present invention to substitute for detergents. However, it is preferable to use detergents rather than high concentrations of salt.

The present invention thus provides a fast and simple method of extracting viruses from a cell culture. The detergent can be added directly to a suspension culture or to the medium of adherent cells. In either case, the medium does not need to be removed first. Furthermore, no other means of disrupting cells or extracting viruses is necessary, such as freeze-thawing or sonication.

An important feature of the present invention is that the extraction procedure can be performed at or above ambient temperature. Traditionally, virus extraction and purification are carried out at a low temperature, typically 0–4° C., to preserve the structures and functions of proteins. For the same reason, protease inhibitors are usually also included in the extraction solutions. Therefore, it is surprising that the present protocol can be conducted at a higher temperature without any protease inhibitor. In fact, a temperature as high as 37° C. resulted in about the same amount of infectious virus as 25° C. Consequently, virus extraction can be carried out by adding a detergent directly to the cell culture and continuing to agitate the culture in order to release the virus, without having to change the temperature. Alternatively, since there is no need to maintain a constant temperature for virus extraction according to the present invention, the procedure can take place at ambient temperature even though ambient temperature may vary from place to place or with time in the same place.

Subsequent to extraction, the virus can be purified based on, for example, the size or density difference between the virus and the other constituents in the extract. Particularly, filtration or centrifugation can be employed to remove cell debris from the virus. To optimize filtration conditions, we tested the effect of various filters in the presence of several different extraction detergents (Example 1). A step-wise filtration protocol proved to be the most effective. Thus, a pre-filter having a relatively large pore size (e.g., 5 μM or 8 μM) is first used to remove large pieces from the extraction mixture, followed by filters with small pore sizes, such as a combination filter unit containing a 3 μM filter and a 0.8 μM filter. In the absence of pre-filters, the extraction mixture would clog the filter quickly, thereby wasting both material and time.

Based on the volume collected after filtration, as shown in Example 1, it is preferable to use 1% TRITON® X-100 for virus extraction. In addition, cellulose acetate membrane filters are better than glass fiber membrane filters, because the cellulose acetate membrane filter allows a higher volume of extraction mixture to be filtered, rendering it more suitable for large-scale production.

Depending on the purpose of virus production, it may be desirable to concentrate the virus-containing filtrate. A concentration step using ultrafiltration/diafiltration is demonstrated in Example 2. Two ultrafiltration/diafiltration systems were tested, the Plate and Frame Cassette of Pall Filtron and the Hollow Fiber Cartridge of A/G Technology. The results show that the two systems are comparable in their speed of operation or the extent of volume loss, but the Hollow Fiber Cartridge is easier to handle.

The virus may be further purified based on its surface charge. Since different viruses have different surface proteins, which dictate their surface charge at any given pH, the appropriate condition for purification will have to be decided for each virus. Example 3 illustrates a determination of optimal ion exchange conditions for reovirus. Thus, ion exchange columns containing different resins were used at different pH to purify a reovirus preparation that has been extracted, filtered and concentrated as described above. The results indicate that a weak anion column containing ANX SEPHAROSE™ at pH 7.0–8.5 is the most effective. The pH is more preferably about 7.5 or 8.0, and most preferably about 8.0.

The virus may also be purified based on the difference in size, for example, with size exclusion chromatography. For reovirus, a combination of ion exchange and size exclusion chromatography is particularly effective. Other chromatographic methods, such as those based on affinity or hydrophobic interaction, can also be used where appropriate. Therefore, column chromatography can be adopted as an effective alternative to CsCl density gradient ultracentrifugation to achieve good yield, purity and scalability.

The present method can be applied to reovirus production using cells other than HEK 293 cells, including but not limited to, mouse L929, Vero and Chinese hamster ovary cells. It is contemplated that the present method be applied to other viruses as well, particularly the other non-enveloped viruses. Appropriate conditions for the purification of other viruses can be determined by a person of ordinary skill in the art based on the disclosure herein. The viruses that can be prepared using the present method include, but are not limited to, the viruses in the families of myoviridae, siphoviridae, podpviridae, teciviridae, corticoviridae, plasmaviridae, lipothrixviridae, fuselloviridae, poxviridae, iridoviridae, phycodnaviridae, baculoviridae, herpesviridae, adnoviridae, papovaviridae, polydnaviridae, inoviridae, microviridae, geminiviridae, circoviridae, parvoviridae, hepadnaviridae, retroviridae, cyctoviridae, reoviridae, birnaviridae, paramyxoviridae, rhabdoviridae, filoviridae, orthomyxoviridae, bunyaviridae, arenaviridae, leviviridae, picornaviridae, sequiviridae, comoviridae, potyviridae, caliciviridae, astroviridae, nodaviridae, tetraviridae, tombusviridae, coronaviridae, glaviviridae, togaviridae, and barnaviridae.

Compositions

Also provided are compositions comprising the virus prepared according to methods of the present invention. These compositions can be used in the isolation and characterization of viral proteins, production of vaccines, or, where the composition contains infectious virus, as virus stocks or in clinical administration.

For the purpose of clinical administration, the composition is usually mixed with an excipient, diluted by an excipient or enclosed within such a carrier which can be in the form of a capsule, sachet, paper or other container (WO99/08692A1) as a pharmaceutical composition. When the pharmaceutically acceptable excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, sterile saline, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the invention can be formulated so as to provide quick, sustained or delayed release of the active ingredient after administration to the patient by employing procedures known in the art.

The route by which the reovirus is administered, as well as the formulation, carrier or vehicle, will depend on the location as well as the type of the target cells. A wide variety of administration routes can be employed. For example, for a solid neoplasm that is accessible, the reovirus can be administered by injection directly to the neoplasm. For a hematopoietic neoplasm, for example, the reovirus can be administered intravenously or intravascularly. For neoplasms that are not easily accessible within the body, such as metastases, the reovirus is administered in a manner such that it can be transported systemically through the body of the mammal and thereby reach the neoplasm (e.g., intravenously or intramuscularly). Alternatively, the reovirus can be administered directly to a single solid neoplasm, where it then is carried systemically through the body to metastases. The reovirus can also be administered subcutaneously, intraperitoneally, intrathecally (e.g., for brain tumor), topically (e.g., for melanoma), orally (e.g., for oral or esophageal neoplasm), rectally (e.g., for colorectal neoplasm), vaginally (e.g., for cervical or vaginal neoplasm), nasally or by inhalation spray (e.g., for lung neoplasm). Preferably, the reovirus is administered by injection.

The liquid forms in which the pharmaceutical compositions of the present invention may be incorporated for administration orally or by injection include aqueous solutions, suitably flavored syrups, aqueous or oil suspensions, and flavored emulsions with edible oils such as corn oil, cottonseed oil, sesame oil, coconut oil, or peanut oil, as well as elixirs and similar pharmaceutical vehicles.

For preparing solid compositions such as tablets, the principal active ingredient/reovirus is mixed with a pharmaceutical excipient to form a solid preformulation composition containing a homogeneous mixture of a compound of the present invention. When referring to these preformulation compositions as homogeneous, it is meant that the active ingredient is dispersed evenly throughout the composition so that the composition may be readily subdivided into equally effective unit dosage forms such as tablets, pills and capsules.

The tablets or pills of the present invention may be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described herein. Preferably the compositions are administered by the oral or nasal respiratory route for local or systemic effect. Compositions in preferably pharmaceutically acceptable solvents may be nebulized by use of inert gases. Nebulized solutions may be inhaled directly from the nebulizing device or the nebulizing device may be attached to a face mask tent, or intermittent positive pressure breathing machine. Solution, suspension, or powder compositions may be administered, preferably orally or nasally, from devices which deliver the formulation in an appropriate manner.

Another preferred formulation employed in the methods of the present invention employs transdermal delivery devices ("patches"). Such transdermal patches may be used to provide continuous or discontinuous infusion of the reovirus of the present invention in controlled amounts. The construction and use of transdermal patches for the delivery of pharmaceutical agents is well known in the art. See, for example, U.S. Pat. No. 5,023,252, herein incorporated by reference. Such patches may be constructed for continuous, pulsatile, or on demand delivery of pharmaceutical agents.

Other suitable formulations for use in the present invention can be found in *Remington's Pharmaceutical Sciences*.

The following examples are offered to illustrate this invention and are not to be construed in any way as limiting the scope of the present invention.

EXAMPLES

In the examples below, the following abbreviations have the following meanings. Abbreviations not defined have their generally accepted meanings.

| | |
|---|---|
| CI = | Confidence Interval |
| $TCID_{50}$ = | Tissue Culture Infectious $Dose_{50}$ |
| μM = | micromolar |
| mM = | millimolar |
| M = | molar |
| ml = | milliliter |
| μl = | microliter |
| mg = | milligram |
| μg = | microgram |
| g/L = | grams per liter |
| rpm = | revolutions per minute |
| FBS = | fetal bovine serum |
| DTT = | dithiothrietol |
| NP-40 = | NONIDET ™ P-40 (Octylphenoxy Polyethoxy Ethanol) |
| SDS = | sodium dodecyl sulfate |
| PBS = | phosphate buffered saline |
| β-ME = | β-mercaptoethanol |
| MOI or m.o.i. = | multiplicity of infection |
| PFU = | plaque forming units |
| hr = | hour |
| ° C. = | degree Celsius |

General Materials and Methods

Cells and Virus

Human embryo kidney 293 (HEK 293) and mouse fibroblast L-929 cells were provided by the manufacturer BioReliance Corporation (Rockville, Md.). HEK 293 cells were grown in a culture medium containing 10% heat-inactivated horse serum and 90% of the following mixture: Eagle's minimum essential medium with 2 mM L-glutamine and Earle's Balanced Salt Solution adjusted to contain 1.5 g/L sodium bicarbonate, 0.1 mM non-essential amino acids, and 1.0 mM sodium pyruvate. Mouse L-929 cells were propagated in a culture medium containing 10% FBS and 90% of the following mixture: Eagle's minimum essential medium with 2 mM L-glutamine and Earle's Balanced Salt Solution adjusted to contain 1.5 g/L sodium bicarbonate, 0.1 mM non-essential amino acids, and 1.0 mM sodium pyruvate.

The 293/SF cells were grown in 293 Serum Free Medium (Life Technologies, Rockville, Md.) supplemented with 4 mM L-glutamine at 36° C.±2° C., 6%±2% $CO_2$ and 80%±5% relative humidity in spinner flasks at an impeller speed of 35–40 rpm.

The Dearing strain of reovirus serotype 3 used in these studies was first propagated in suspension cultures of L-929 cells purified according to Smith (Smith et al., 1969) with the exception that β-mercaptoethanol (β-ME) was omitted from the extraction buffer. The particle/PFU ratio for purified reovirus was typically 100/1. Viral titers were determined by plaque titration on L-929 cells and expressed as $Log_{10}TCID_{50}$/ml. The virus was then produced in large scale in 293/SF cells.

Infection of Suspension Cells

293/SF cells were grown to $10^6$/ml and infected with the reovirus. The culture was allowed to grow until the color of the medium turned from red to orange, or until the viability of the cells dropped to the desired level as evidenced by a viable cell count. Viable cell counts can be performed under the microscope for cells that do not show a cytopathic effect, which is indicated by the cells becoming swollen and granular in appearance and the cell clumps breaking apart. Viable cell counts can also be performed by a viable stain as commonly used in the art.

Traditional Method of Extraction and Purification of Virus

When the desired cell viability level was reached, the cells were pelleted in a centrifuge and resuspended in 10 mM Tris, pH C17.4, 250 mM NaCl and 0.1% TRITONT® X-100. The cells were then lysed by freeze-thawing and kept on ice for 20–40 minutes with periodical vortexing to mix and lyse the cells. The suspension was extracted with an equal volume of pre-chilled FREON® (1,1,2-trichloro- 1,1, 2-trifluoro-ethane) by vortexing for 10 minutes, followed by centrifugation at 2500 rpm for 10 minutes at 40° C. to separate the difference phases. The aqueous (top) phase was removed and re-extracted twice as described above, and the virus was pelleted by ultracentrifugation at 25,000 rpm for one hour at 40° C.

The pellet was resuspended in PBS and the virus was purified by a cesium chloride step gradient. The gradient contained two layers of CsCl solutions (1.20 g/ml and 1.4 g/ml, respectively) prepared in 10 mM Tris (pH 7.4). The virus suspension was loaded on top of the gradient and centrifuged in a SW 28.1 rotor at 26,000 rpm for 2 hours at 4° C. The viral band (the lower of the two bands because the upper band contained empty capsids) was harvested and dialyzed against sterile PBS.

BENZONASE® Endonuclease Treatment

After lysing the cells with a detergent, a solution of 50 mM $MgCl_2$ was added to the crude lysate to a final concentration of 1 mM $MgCl_2$. BENZONASE® endonuclease (250,000 units/ml, EM Industries Catalog No. 1016979M) was then added to approximate 10 units/ml. The lysate was agitated in an incubator at 36° C. for an hour.

Example 1

Clarification: Removing Cell Debris

The purpose of this Example was to develop a suitable clarification procedure that is both compatible with the protocol using detergents to lyse cells and amenable to future scale-up and manufacturing. In this Example, the lysate was filtered either through a 3 μm/0.8 μm capsule filter or passed through a combination of a pre-filter (5 μm or 8 μm) and then a 3 μm/0.8 μm capsule filter. All the filters used in this study had a surface area of 0.015 ft$^2$. Based on the volume filtered through the 0.015 ft$^2$ membrane, the capacity of the membranes was determined for large-scale filtration. Also, filtration efficiency was compared for two different membrane materials—cellulose acetate and glass fiber membrane for the 3 μm/0.8 μm capsule filter.

Three detergents were tested. Reovirus-harboring cells were divided equally into three sterile 1 L bottles labeled for the three different lysis agents to test: 1% TRITON® X-100, 0.3% TRITON® X-100 and 0.1% Na-DOC. A volume of 92 mL and 28 mL of 10% TRITON® X-100 was added to bottles 1 and 2 so that the working concentrations in these bottles were 1% and 0.3% TRITON® X-100, respectively. A volume of 9.2 mL of 10% Na-DOC was added to the third bottle to a working concentration of 0.1%. All the three bottles were placed on a stir plate and agitated at 160±20 rpm for 30 minutes at room temperature. A post-lysis sample was taken for each lysis condition for titer analysis.

About 20 mL of 50 mM MgCl$_2$ was added to the crude lysate in each of the bottles to a working concentration of approximately 1 mM MgCl$_2$. This was followed by addition of 40μL BENZONASE® endonuclease (250,000 units/mL) to a working concentration of approximately 10 units/mL. The crude lysate was agitated at setting 5 in an incubator at 36° C. for one hour. These steps were included to remove host cell DNA and to reduce viscosity of the lysate, thereby facilitating ease of further processing.

The Watson-Marlow pump (505U) was calibrated to relate flow rate to the pump speed. According to suggestions by the vendor, a pump speed of 5 rpm (40 mL/min flow rate) was used throughout the clarification study.

The lysate from each treatment condition was passed through one of the following filters:

1) 3 μm/0.8 μm capsule filter;
2) A pre-filter 5 μm size→3 μm/0.8 μm capsule filter connected in series; and
3) A pre-filter of 8 μm membrane pore size 3 μm/0.8 μm capsule filter connected in series.

The 3 μm/0.8 μm capsule filters have a double layer heterogeneous membrane construction that allows for high dirt loading capacity and increased throughput. The first filter is of a larger pore size (3 μm) than the second filter (0.8 μm). The pre-filters combine multiple layers of progressively finer pleated non-woven polypropylene depth filter material. All the filters used in this study had a surface area of 0.015 ft$^2$. Two membrane materials, namely cellulose acetate and glass fiber, were tested for the 3 μm/0.8 μm capsule filters.

The best combination of lysis agent and filter conditions was determined based on titer values and the volumes passed through the filters. Pressure drop across the membranes was monitored to determine when membrane fouling occurred. The indication for membrane fouling was a pressure drop of 25 psi, beyond which the filter can break. When the 3μm/0.8μm capsule filter was used alone, no more than 35 mL passed through these capsule filters before the membrane fouled. Membrane size 3/0.8 μm fouled within 5 minutes, suggesting that use of a pre-filter was necessary to eliminate clotting of the membranes by cellular debris. Use of a 5μm pre-filter before the 3/0.8μm capsule filter significantly increased the amount of filtrate obtained, while filtration through a 8μm pre-filter followed by 3μm/0.8μm capsule filtration gave the highest membrane capacity in terms of volume passed through the filters (an average of 200 mL was collected per 0.015 ft$_2$ of filter surface area). 1% TRITONT® X-100 gave the best results compared to the other two lysis conditions.

The results also show that the cellulose acetate membrane material worked better than the glass fiber membrane, based on the volume filtered through these membranes. No significant loss of infectivity was observed at any stage of filtration when compared to infectivity of the bulk harvest (cell culture before lysis and filtration). Based on the results from this study, a 20 L bulk harvest would require 1.5 ft$^2$ of membrane surface area for filtration.

Example 2

Concentration

To select a suitable system to concentrate and diafilter the clarified lysate, the Plate and Frame cassette from Pall Filtron and the Hollow Fiber cartridge from A/G Technology were compared. The same polyethersulfone membrane material was used in both systems. The criteria for selection were the ease of use, extent of concentration achieved and the virus titer of the product.

The Plate and Frame cassette used in this study was Pall's MINIM system, which is a laboratory benchtop unit, and the LV Centramate containing two suspended screen channel 300 kD Ultrafiltration Membranes (0.2 ft$^2$ each). Prior to concentrating the clarified lysate, the apparatus was rinsed with 2 L of Reverse Osmosis (RO) water (USP grade) to flush out the storage gel. The cassettes were sanitized with 2 L of warmed 0.1N NaOH. The system was then drained, rinsed with 2 L of RO water and conditioned with the growth medium for the virus. The whole system was drained and the hold-up volume of the system and tubing was determined to be 6 mL.

The Hollow Fiber cartridge tested in this study was MG Technology's QUIXSTAND™ Benchtop System, Size 4M column Ultrafiltration Cartridge (650 cmsurface area). As with Plate and Frame cassette, the apparatus was first flushed with 2 L of Reverse Osmosis (RO) water (USP grade) to flush out the storage gel. The cassettes were sanitized with 2 L of warmed 0.1N NaOH. The system was then drained, rinsed with 2 L of RO water and conditioned by flushing with the growth medium of the virus. A constant Feed Flowrate of 600 mL/min was used throughout the experiment.

For both systems, the clarified lysate was recirculated until the material was concentrated to ~250 mL (10×concentration), and a sample was taken for titer analysis (Post I-Concentration). The concentrate (retentate) was diafiltered against 1 L (5 diafiltration volumes) of Diafiltration Buffer (20 mM Tris+0.2M NaCl+1 mM MgCl$_2$, pH 8.0±0.1), and another sample was taken for titer analysis (Post-Diafiltration). The retentate was further concentrated to about 120 mL. Following the final concentration, the product was drained from the system and collected in a single, sterile container (Post-final Concentration). The system was then rinsed with 40 mL of Diafiltration Buffer to ensure maximum product recovery.

The process parameters monitored during the concentration process with both the hollow fiber and plate and frame systems are shown in Table 1.

TABLE 1

Comparison of Process Parameters for the Hollow Fiber and Plate and Frame Systems

| System | Process Time (hr) | Surface Area (cm$^2$) | Concentration Factor | Average Feed Flow rate (mL/min) start | Average Feed Flow rate (mL/min) end | Permeate Flow Rate ml/min start | Permeate Flow Rate ml/min end | TMP (psi) start | TMP (psi) end |
|---|---|---|---|---|---|---|---|---|---|
| Hollow Fiber | 3 | 650 | 14X | 600 | 600 | 50 | 18 | 8 | 8 |
| Plate and Frame | 4 | 372 | 20X | 260 | 450 | 54 | 12 | 9.2 | 30 |

TMP = [(Feed Pressure + Retentate Pressure)/2 − Permeate Pressure]

The Transmembrane Pressure (TMP) stayed at less than 8 psi throughout the hollow fiber process, while the TMP rose to 30 psi with the plate and frame process. The use of more membrane surface area for the hollow fiber system probably resulted in less fouling of the cartridge.

About 20×fold-concentration was achieved with the Plate and Frame cassette in 4 hours, while a 14×fold-concentration was obtained using the Hollow Fiber Cartridge in 3 hours and we could have obtained 20×concentration in another 30 minutes. There was 45–50% loss of the product when compared to the post-lysis values with either system. The set-up of the Hollow Fiber Cartridge was easier than the Plate and Frame Cassette. Therefore, the Hollow Fiber Cartridge is the suitable system for ultrafiltration and diafiltration steps based on ease of handling.

Example 3
Ion Exchange

Viruses have different surface charges due to their surface molecules. Therefore, it is possible to purify viruses using ion exchange chromatography, and the conditions will vary depending on the nature of the viruses. Accordingly, we tested ion exchange chromatography conditions of various pHs for reovirus. Reovirus was produced, extracted and filtered as described above and subjected to ion exchange chromatography at different pH. The titer after each step was determined and listed below.

TABLE 2

The effects of ion exchange chromatography at various pH

| Sample | Titer ± 95% CI (Log$_{10}$TCID$_{50}$/ml) | Volume Correction[2] | Corrected Titer ± 95% CI (Log$_{10}$TCID$_{50}$/ml) |
|---|---|---|---|
| Spiking Virus Control, Oct. 30, 2001 | 8.05 ± 0.47 | — | — |
| Certified Titer of RE3013101P | 8.35 ± 0.27 | — | — |
| Negative Control | No virus detected | — | — |
| ONC 101, Bulk harvest | ** | — | — |
| ONC 102, Post filtration | 9.18 ± 0.36 | — | 9.18 ± 0.36 |
| ONC 103, Post Column, Strong Cation pH 4.0 | 5.93 ± 0.24 | 1.02 | 5.94 ± 0.24 |
| ONC 104, Post Column, Strong Cation pH 5.0 | 8.93 ± 0.42 | 1.01 | 8.93 ± 0.42 |
| ONC 105, Post Column, Strong Cation pH 6.0 | 9.18 ± 0.40 | — | 9.18 ± 0.40 |
| ONC 106, Post Column, Strong Cation pH 7.0 | 9.30 ± 0.37 | — | 9.30 ± 0.37 |
| ONC 107, Post Column, Strong Cation pH 8.0 | 9.55 ± 0.32 | — | 9.55 ± 0.32 |
| ONC 108, Post Column, Weak Cation pH 4.0 | 8.93 ± 0.40 | 1.01 | 8.93 ± 0.40 |
| ONC 109, Post Column, Weak Cation pH 5.0 | 9.18 ± 0.36 | 1.01 | 9.18 ± 0.36 |
| ONC 110, Post Column, Weak Cation pH 6.0 | 8.68 ± 0.40 | — | 8.68 ± 0.40 |
| ONC 111, Post Column, Weak Cation pH 7.0 | 9.30 ± 0.37 | — | 9.30 ± 0.37 |
| ONC 112, Post Column, Weak Cation pH 8.0 | 8.18 ± 0.36 | 1.02 | 8.19 ± 0.36 |
| ONC 113, Post Column, Strong Anion pH 5.0 | 5.30 ± 0.37 | 1.01 | 5.30 ± 0.37 |
| ONC 114, Post Column, Strong Anion pH 6.0 | 4.80 ± 0.00 | — | 4.80 ± 0.00 |
| ONC 115, Post Column, Strong Anion pH 7.0 | 7.80 ± 0.35 | — | 7.80 ± 0.35 |
| ONC 116, Post Column, Strong Anion pH 8.0 | 10.18 ± 0.36 | 1.01 | 10.18 ± 0.36 |
| ONC 117, Post Column, Strong Anion pH 9.0 | 8.55 ± 0.32 | — | 8.55 ± 0.32 |
| ONC 118, Post Column, Weak Anion pH 5.0 | 7.93 ± 0.40 | — | 7.93 ± 0.40 |
| ONC 119, Post Column, Weak Anion pH 6.0 | 6.68 ± 0.40 | — | 6.68 ± 0.40 |
| ONC 120, Post Column, Weak Anion pH 7.0 | 8.30 ± 0.37 | 1.02 | 8.31 ± 0.37 |
| ONC 121, Post Column, Weak Anion pH 8.0 | 10.53 ± 0.36 | 1.03 | 10.54 ± 0.36 |
| ONC 122, Post Column, Weak Anion pH 9.0 | 8.93 ± 0.24 | 1.03 | 8.94 ± 0.24 |

Accordingly, pH 7.0–9.0 resulted higher yield of reovirus than other pHs. The pH used in this step is preferably 7.5–8.5, particularly pH 8.0. Although both cation and anion exchangers worked, anion exchangers were generally more effective.

I claim:

1. A method of producing virus from a culture of cells, comprising the steps of:
   (a) providing a culture of mammalian cells in suspension which has been infected by the virus in culture;
   (b) extracting the virus from the cells by adding a detergent to the culture of mammalian cells in suspension and incubating for a period of time to result in a cell lysate;
   (c) separating cell debris from the virus in the cell lysate by step-wise filtration comprising:
      (i) filtering through a prefilter having a pore size of 5 μM or 8 μM, and
      (ii) filtering after step (i) through a combination filter having pore sizes of 3 μM and 0.8 μM;
   (d) purifying the virus by a combination of ion exchange and size exclusion chromatography; and
   (e) collecting the virus,
   provided that after infection by the virus and before extraction of the virus, the mammalian cells are not pelleted or resuspended.

2. The method of claim 1 further comprising treating the cell lysate with a DNA-cleaving enzyme.

3. The method of claim 1 further comprising concentrating the filtrate.

4. The method of claim 1 wherein the virus is a non-enveloped virus.

5. The method of claim 1 wherein the virus is a reovirus.

6. The method of claim 1 wherein the cells are human embryo kidney 293 (HEK 293) cells.

7. The method of claim 1 further comprising purifying the virus by anion exchange chromatography.

8. The method of claim 3 wherein the filtrate is concentrated by diafiltration.

9. The method of claim 5 wherein the reovirus is a recombinant reovirus.

10. The method of claim 5 wherein the reovirus is a mammalian reovirus.

11. The method of claim 10 wherein the mammalian reovirus is a human reovirus.

12. The method of claim 11 wherein the human reovirus is a serotype 3 virus.

13. The method of claim 12 wherein the serotype 3 reovirus is the Dearing strain.

14. A method of producing infectious reovirus, comprising:
   (a) providing a culture of HEK 293 cells in suspension which has been infected by reovirus in culture;
   (b) extracting the reovirus from the HEK 293 cells by adding octoxynol-9 to 10 to the culture of HEK 293 cells in suspension and incubating at about 25° C. to about 37° C.;
   (c) treating the mixture from step (b) with a DNA-cleaving enzyme;
   (d) separating cell debris from the reovirus in the mixture from step (c) by step-wise filtration comprising:
      (i) filtering through a prefilter having a pore size of 5 μM or 8 μM, and
      (ii) filtering after step (i) through a combination filter having pore sizes of 3 μM and 0.8 μM;
   (e) concentrating the filtrate by ultrafiltration or diafiltration;
   (f) purifying the reovirus by a combination of ion exchange and size exclusion chromatography; and
   (g) collecting the reovirus,
   provided that after infection by the reovirus and before extraction of the reovirus, the HEK 293 cells are not pelleted or resuspended.

* * * * *